(12) United States Patent
Voumard (10) Patent No.: US 10,955,397 B2
(45) Date of Patent: Mar. 23, 2021

(54) GAS MEASUREMENT DEVICE INCORPORATED INTO A WATCH

(71) Applicant: TAKE OFF DIFFUSION S.A., La Neuveville (CH)

(72) Inventor: Olivier Voumard, Le Landeron (CH)

(73) Assignee: TAKE OFF DIFFUSION S.A.

( * ) Notice: Subject to any disclaimer, the term of this patent is extended or adjusted under 35 U.S.C. 154(b) by 0 days.

(21) Appl. No.: 15/751,884

(22) PCT Filed: Aug. 10, 2016

(86) PCT No.: PCT/IB2016/001104
§ 371 (c)(1),
(2) Date: Feb. 12, 2018

(87) PCT Pub. No.: WO2017/025791
PCT Pub. Date: Feb. 16, 2017

(65) Prior Publication Data
US 2018/0231515 A1 Aug. 16, 2018

(30) Foreign Application Priority Data
Aug. 13, 2015 (CH) ..................... 01160/15

(51) Int. Cl.
*G01N 33/00* (2006.01)
*G04G 21/02* (2010.01)
(Continued)

(52) U.S. Cl.
CPC ....... *G01N 33/0063* (2013.01); *G01N 33/004* (2013.01); *G01N 33/0044* (2013.01);
(Continued)

(58) Field of Classification Search
CPC .................. G04G 21/02; G04B 47/06–068
See application file for complete search history.

(56) References Cited

U.S. PATENT DOCUMENTS

| 7,129,827 B2 * | 10/2006 | Bai ........................ G01H 1/003 340/438 |
| 8,144,547 B2 * | 3/2012 | Plancon ............... G04B 19/082 368/10 |

(Continued)

FOREIGN PATENT DOCUMENTS

| EP | 1293946 | 3/2003 |
| GB | 2331363 | 5/1999 |

*Primary Examiner* — Edwin A. Leon
*Assistant Examiner* — Jason M Collins
(74) *Attorney, Agent, or Firm* — Galbreath Law Offices, P.C.; John A. Galbreath (57) ABSTRACT

A device for measuring the concentration of a gas constituting the ambient air includes a wristwatch comprising a watch case (13) containing a watch movement, members indicating the time (1, 3, 9) visible through a glass of the watch case (13). In addition, the wristwatch comprises at least one sensor (11) arranged to measure the concentration of a gas constituting the ambient air. The wristwatch also includes means for actuating an alert when reaching or exceeding a threshold of the gas concentration measured by the sensor (11). The device includes two operating states, a "time" state and an "alarm" state, wherein in the "time" state, the members indicating the time (1, 1', 3, 9) indicate the time and the sensor (11) permanently measures the gas concentration without displaying it or activating the alert. In case where the sensor (11) detects a concentration of a gas, the device switches to the "alert" state wherein the indicator member (4, 4', 8, 9, 10) displays this measured value and/or the means for actuating an alert actuate an alert normally without the time being displayed.

15 Claims, 7 Drawing Sheets

(51) Int. Cl.
*G04G 9/00* (2006.01)
*G08B 21/14* (2006.01)
*G08B 21/18* (2006.01)

(52) U.S. Cl.
CPC ........... *G04G 9/0005* (2013.01); *G04G 21/02* (2013.01); *G08B 21/14* (2013.01); *G08B 21/182* (2013.01)

(56) References Cited

U.S. PATENT DOCUMENTS

| | | | |
|---|---|---|---|
| 2003/0052792 A1* | 3/2003 | Koyano | G08B 21/14 340/632 |
| 2004/0066300 A1* | 4/2004 | Dorenbosch | G04C 10/04 340/636.1 |
| 2010/0074059 A1 | 3/2010 | Takayuni | |
| 2011/0034792 A1 | 2/2011 | Williams | |
| 2013/0033970 A1* | 2/2013 | Miyake | G04C 3/146 368/80 |
| 2013/0064045 A1* | 3/2013 | Essery | H04W 88/02 368/47 |
| 2016/0195855 A1* | 7/2016 | Mirza | G04R 20/08 368/10 |
| 2016/0341568 A1* | 11/2016 | Roush | G01C 22/006 |
| 2016/0357354 A1* | 12/2016 | Chen | H04M 1/72569 |

\* cited by examiner

GAS MEASUREMENT DEVICE INCORPORATED INTO A WATCH

The present invention relates to gas measuring devices.

The dangers due to gases can have different origins such as a leak of one or more toxic gases, a defect or a too high concentration of oxygen, or the presence of flammable gases. If it is not detected early, staff, premises and equipment cannot be protected.

Depending on the need, it may be necessary to choose a detector which is very specific or on the contrary capable of detecting a wide variety of gases.

The main risks that arise from the presence of gas are an explosion due to the presence of flammable gases and an intoxication or an asphyxiation due to the presence of toxic gases.

A gas detector may therefore prove to be necessary as an individual protection for activities exposed to a risk. Portable gas detectors can meet one-off business needs, or in many industrial applications, safety must be continuously ensured by a stationary gas detection system.

The need to measure at the same time and continuously the concentration of several gases is increasingly frequent in industrial applications (chemical and agri-food industries but also boiler rooms, tunnels . . . )

Toxic gases come from diverse sources, such as combustion (CO—NO—NO2-SO2), incineration (H2S—NH3-HCl) or fermentation (H2S—NH3).

Their passive or active presence in an industrial environment is frequent (chemicals, petrochemicals, cold chains, agri-food) and makes their detection essential. The risks of intoxication are related to the exposure time of a subject to a harmful product. The danger is assessed in terms of average exposure value and exposure limit value. These values are expressed both in weight (mg/m3) and in volume (part per million, ppm).

The portable gas detectors allow knowing if the ambient atmosphere is explosive or not, which is fundamental for the safety of the first responders on a fire for example. The danger of explosion caused by a particular gas is often underestimated and the responder must rely on an apparatus for detecting and measuring the explosiveness that is compact, reliable and easy to implement.

The main drawback of these portable apparatuses is that they must be brought to an unsafe place and often deposited as soon as the risk area is left. Therefore, a person may find himself/herself in an area that is presumed to be safe, such as his/her home, and be exposed to the presence of a toxic gas such as carbon monoxide.

The aim of the present invention is to propose an alternative to all these apparatuses, and more particularly, to propose a wristwatch including a gas detector that allows measuring the gas concentration in the risk areas, as in the areas that are thought to be safe.

In accordance with the invention, a device for measuring the concentration of a gas constituting the ambient air includes a wristwatch comprising a watch case containing a watch movement, members indicating the time visible through a glass of the watch case. Furthermore, the wristwatch comprises at least one sensor arranged to measure the concentration of a gas constituting the ambient air, this sensor being located in a housing of the watch case or of an element attached to the watch case and having a surface inside this housing exposed to the ambient air through at least one hole, the hole being on a part of the watch case or on the attached element that is not in contact with the wearer's wrist when the wristwatch is worn on the wrist. The wristwatch also includes a member indicating the measured value of the gas concentration, this indicator member allowing to know the value of the instantaneously measured gas concentration. It also includes means for actuating an alert.

According to the invention, the device includes two states (or "modes") of operation, a "time" state and an "alarm" state, wherein in the "time" state the members indicating the time indicate the time and the sensor continuously measures the gas concentration without displaying it and without actuating an alert in the absence of measured gas concentration. In case the sensor detects a gas concentration when the sensor is in the "time" state, the device switches to the "alert" state wherein the members indicating the time are preferably inactivated, and the member indicating the measured value of the gas concentration displays this measured value and/or the means for actuating an alert actuate an alert when reaching or exceeding a threshold of the gas concentration measured by the sensor. In case the sensor does no longer detect a gas concentration when it is in the "alert" state, the device switches to the "time" state.

In an embodiment, the member indicating the measured value of the gas concentration may also indicate the maximum value of the measured gas concentration.

In a variant, the wristwatch may include a sensor for measuring the value of the gas concentration measured instantaneously and means for actuating an alert when reaching or exceeding a threshold of the gas concentration measured by the sensor without the wristwatch wearer knowing the reached concentration.

In a preferred embodiment, the watch includes alert means such as for example a light alarm and/or an audible alarm and/or a vibrating alarm.

In a variant, the means of the wristwatch include a wireless communication means allowing to transmit information to another apparatus, in particular a smartphone or a computer, such as for example information that the threshold of the measured gas concentration has been reached or exceeded.

In another embodiment, the wristwatch includes a controller arranged to measure the operating state and/or the lifetime of components integrated in the watch case, in particular the sensor or the lifetime of a power source.

In an embodiment, the wristwatch may include a storage unit arranged to keep a history of the measured values of the gas concentration and optionally the measures of the components integrated in the watch case and inspected by a controller. For example, the watch can record in this storage unit a history of concentrations, exposure durations, gas concentration profiles during an exposure, a maximum of concentration during an exposure, a number of exposures, a lifetime of power sources, a lifetime of the sensor. All this information can be accessible to the user either directly on a display of the watch, or by a remote apparatus such as a smartphone.

According to this embodiment, the means for actuating an alert may be triggered when the controller indicates that at least one component integrated in the watch case requires external intervention.

The wristwatch may include hands for displaying the time and the same hands or other hands for displaying the measured value of the gas concentration In a variant, the wristwatch may include a digital display for displaying the time and the same digital display or another digital display for displaying the measured value of the gas concentration.

In a combined display version, the wristwatch may include hands for displaying the time and a digital display for displaying the measured value of the gas concentration and vice versa.

For ease of maintenance, the wristwatch may include a processing unit capable of receiving information from an external apparatus, for example a smartphone or a PC in order to configure the watch, in particular to benchmark the sensor or to update the time.

In an embodiment, the wristwatch may include, inside the watch case, a transmitter for transmitting information and a receiver for receiving information. Thus, a wireless communication can in particular allow managing the configurations of the watch, transmitting alarms, transferring internal data of the watch such as an initialization and a setting of the watch, a time setting of the watch. Other functions, such as an alarm transmission, a memory data transfer, or a benchmarking and a calibration of a gas sensor can be performed.

Depending on the need, the watch may include a plurality of sensors arranged to measure respectively the concentration of a particular gas constituting the ambient air. The watch may be equipped with sensors for detecting for example hydrogen sulphide, or carbon monoxide.

Furthermore, the inventive device optionally includes a "sleep" state wherein the sensor is deactivated, and at least one push-button, operable when the device is in the "sleep" state in order to activate the device in the "time" state.

The means for actuating an alert can actuate a multi-level alert depending on the gas concentration measured by the sensor, each level of alert corresponding to one or more audible or light beeps or vibrations, of which intensity and frequency may vary.

In some embodiments, the members indicating the time include a dial and at least two hands of different lengths pivoting about an axis, the device further comprising a segment of the dial extending at most over 150° and preferably at most over 120°, this segment of the dial carrying towards its periphery at least two arcuate areas with graduations or other indications concerning a measured gas concentration and/or a maintenance operation, these areas being radially shifted. In this configuration, the hands cooperate with the dial in order to indicate the time in the "time" state, and the hands of different lengths cooperate with the radially shifted arcuate areas during the "alert" state to give at least one indication related to the measured gas concentration and optionally a maintenance indication.

According to an embodiment, the members indicating the time include a dial, the device further comprising a rotary disk whose portion of the circumference can be seen in a window of the dial. The circumference of the disk carries a series of indications related to the measured gas concentration, the operation of the device and/or the lifetime of components integrated in the watch case and/or the lifetime of a power source. The device further includes means for rotating the disk in order to bring a chosen indication to the window and, depending on the chosen indication, to operate the device or to allow calculating different parameters of gas concentration or perform the operations necessary to return the device to the operating condition.

The characteristics of the invention will appear more clearly upon reading the description of several embodiments given only by way of example, in no way restrictive, with reference to the schematic figures, wherein.

Figure 1:
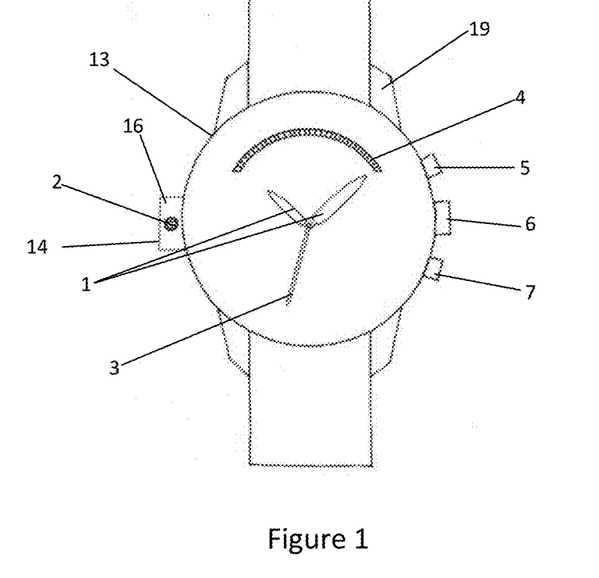
FIG. 1 shows a front view of a wristwatch including a hand display for indicating the time, a hole, for passing the gas towards the sensor, disposed on an element attached to the watch case, wherein a gas sensor is located in order to measure the gas concentration whose value is given on a dedicated indicating scale by means of one of the hands.
Figure 2:
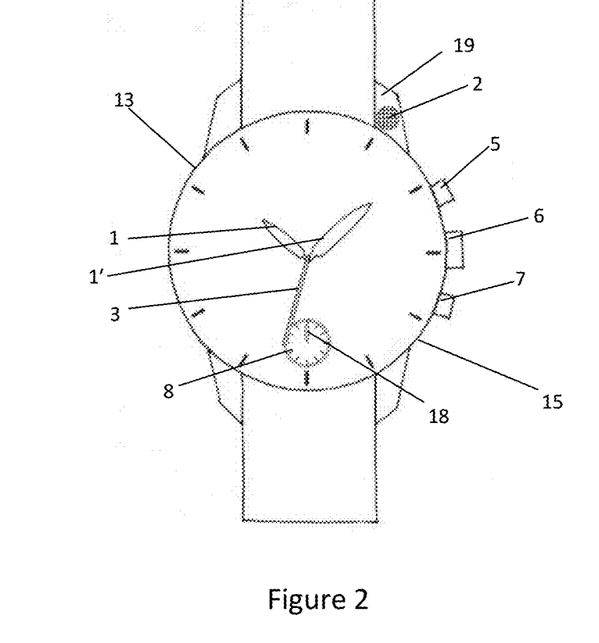
FIG. 2 shows a front view of a wristwatch including a hand display for displaying the time, a hole, for passing the gas towards the gas sensor, disposed on a horn of the watch case, wherein a gas sensor is located in order to measure the gas concentration whose value is given on a remote display by means of another hand.

As illustrated in FIGS. 1 to 7, a wristwatch measures the presence of gas in the ambient air using a sensor 11 disposed, behind a hole 2, inside the watch case 13 (FIG. 7) or on an attached element 14 (FIG. 1) or in a horn 19 of the watch case 13 (FIG. 2).

As illustrated in FIG. 1, the watch, including a watch case 13, and horns 19 for fastening a bracelet, displays the time in a conventional way with hour and minute hands 1, 1' and a second hand 3. The sensor detects the gas through a hole 2 disposed on an element 14 attached to the watch case 13 at 9 o'clock. The hole 2 is located on an outer face 16 of the attached element 14, the hole 2 not being in contact with the wearer's wrist when the wristwatch is worn. A graduated scale 4 indicates the value of the measured gas concentration. The watch includes two push-buttons 5, 7 and a winding crown 6 for setting the time. When the user presses one of the push-buttons 5, 7, an information is transmitted to a microprocessor 17 (FIG. 7) electrically connected to the sensor 11, instructing it to measure the instantaneous gas concentration. Therefore, the second hand 3 indicates on the graduated scale 4 the instantaneous value of the measured gas concentration. When the user presses for the second time the same push-button 5, 7 the second hand 3 resumes its basic function, namely time indication. When the second push-button 5, 7 is activated, the second hand 3 indicates for example the maximum value of the measured gas concentration during the last four hours. This information is stored in the microprocessor 17 and remains accessible on demand. When the threshold of the measured gas concentration has been reached or exceeded, the gas sensor 11 sends an electrical signal to the microprocessor 17 to trigger alert means.

The alert means can for example be a light alarm, an audible alarm, a vibrating alarm, or a wirelessly transmitted alert to a remote apparatus, for example a smartphone, or even to a computer network.

As illustrated in the FIG. 2, the watch displays the time in a conventional way with hour and minute hands 1 and a second hand 3. The sensor detects the gas through a hole 2 disposed on a horn 19 of the watch case 13. A graduated scale 8 at 6 o'clock allows determining the value of the measured gas concentration using a dedicated hand 18. When the threshold of the measured gas concentration has been reached or exceeded, the alert means are triggered.

Figure 3:
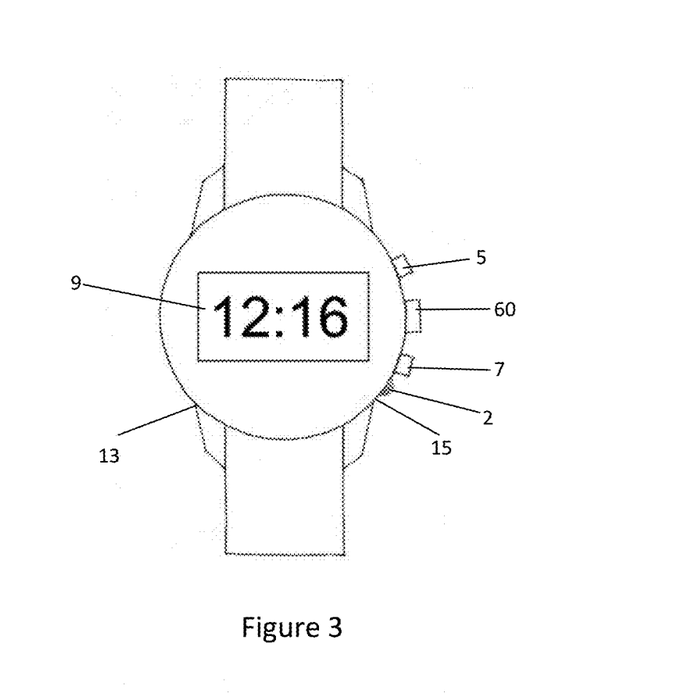
FIG. 3 shows a front view of a wristwatch including a digital display for displaying the time, a hole disposed on the middle band for passing the gas towards the gas sensor in order to measure the gas concentration whose measured gas concentration value is also displayed on the digital display.

As illustrated in FIG. 3, the watch displays the time using a digital display 9. The sensor detects the gas through a hole 2 disposed on the middle band 15 of the watch case 13. The perspective view illustrated in FIG. 6 allows seeing the hole 2 on the middle band 15. The watch includes three push-buttons 5, 60, 7. When the user presses one of the push-buttons 5, 60, 7, the digital display 9 switches on the indication of the value of the measured gas concentration. When the user presses the same push-button 5, 60, 7, the time indication information appears again on the digital display 9. When the threshold of the measured gas concentration has been reached or exceeded, the alert means are triggered and the digital display 9 indicates the measured gas concentration.

Figure 4:
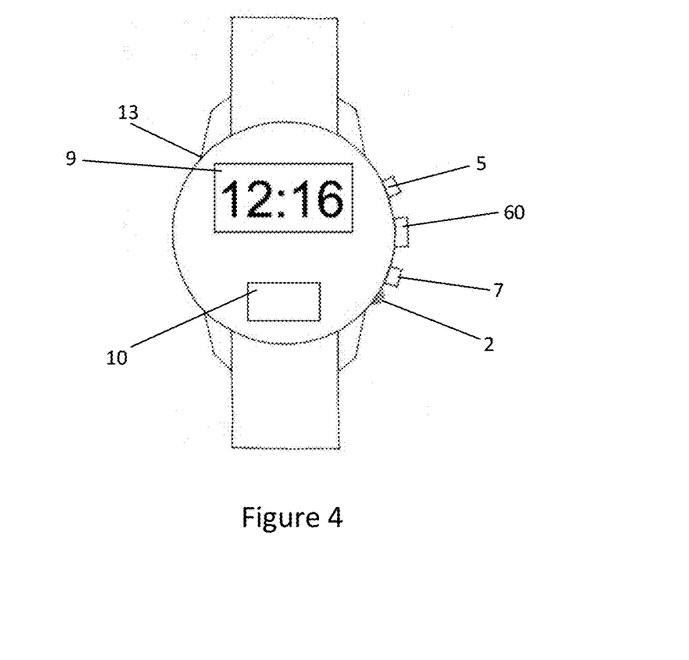
FIG. 4 shows a front view of a wristwatch including a digital display for displaying the time, a hole disposed on the middle band for passing the gas towards the gas sensor in order to measure the gas concentration whose measured gas concentration value is displayed on another digital display.
Figure 5:
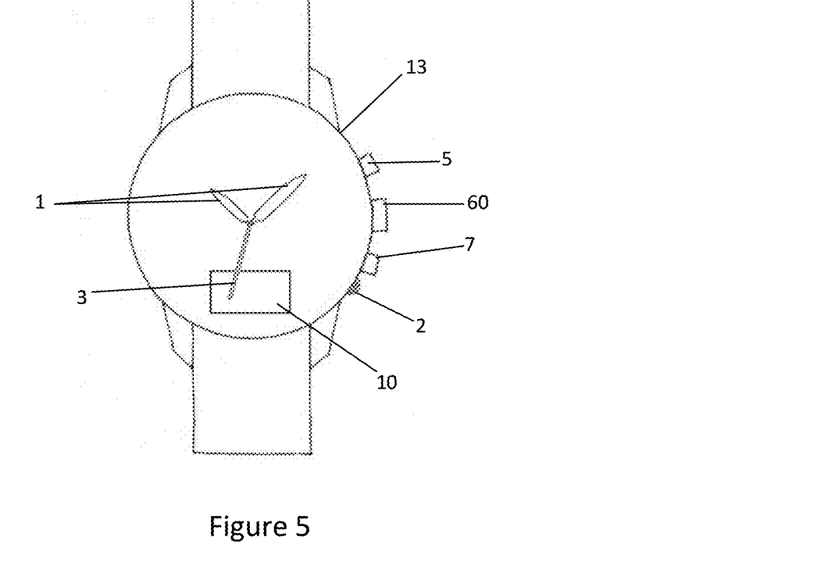
FIG. 5 shows a front view of a wristwatch including a hand display for displaying the time, a disposed hole for passing the gas towards the gas sensor in order to measure the gas concentration whose measured gas concentration value is displayed on a digital display.

The watch illustrated in FIG. 4, displays the time digitally on a first display 9 and the value of the gas concentration also digitally on another digital display 10. The watch includes also three push-buttons 5, 60, 7 for setting the watch and accessing to the additional functions. In the example illustrated in FIG. 5, the watch displays the time with hour and minute hands 1 and second hand 3 and the gas concentration value is digitally indicated on a digital display 10.

Figure 6:
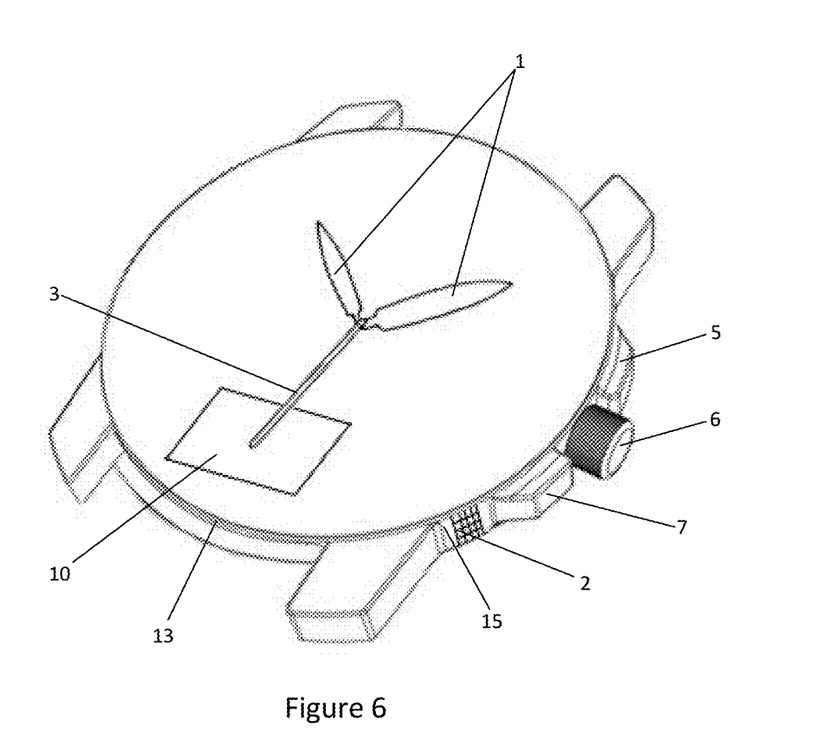
FIG. 6 shows a perspective view of a wristwatch including a hand display for displaying the time, a hole disposed on the middle band of the watch case for passing the gas towards the gas sensor in order to measure the gas concentration whose measured gas concentration value is displayed on a digital display.

The watch illustrated in FIG. 6, includes a hand display for indicating the time and a digital display for the functions of measuring the gas concentration. Among these functions, the watch records in an internal memory, for example of the microprocessor 17 (FIG. 7), the history of the concentrations of the durations of exposure, of the gas concentration profile during an exposure, of the maximum concentration during an exposure, the number of exposures, the lifetime of the batteries, the lifetime of the sensor, the lifetime of the consumables.

The information sent by the sender to the receiver must necessarily pass through a transmission medium. The free space is used as a transmission medium and in this case, it is about wireless transmission. The watch is therefore equipped with a wireless communication system. The wireless communication allows managing the configurations of the watch, transmitting alarms and transferring internal data such as the initialization and the setting of the watch, the setting of the time of the watch, the mode of transmission of the alarms, the transfer of data into memories, the calibration of the gas sensor(s).

The wireless transmission relies on the propagation of electromagnetic waves or airwaves or even radio waves. The radio concept indicates all communication ensured without hardware support, so the term radiocommunication encompasses all wireless communications. The wireless communication can for example be ensured by a communication satellite, by cellular mobile communications, by Wi-Fi, by Bluetooth or by RFID.

In the case of telecommunications satellites, a satellite uses electromagnetic waves or airwaves to connect two terrestrial points, namely the point where the wearer of the watch is located and a point where a monitoring station is located. Telecommunications satellites are used for all kinds of communications: sound broadcasting, television, telephony, data transmission, etc.

In the case of use of Wi-Fi, the watch wearer should be near a router that ensures the connection and operates as a wireless communication hub.

In the case of use of Bluetooth, a protocol that establishes a short-range secure wireless connection between two devices, the watch wearer should be at a distance even closer to the apparatus to which a signal must be transmitted. Bluetooth is similar to Wi-Fi, but the low power used minimizes the range and the available bit rate is generally low.

In the case of use of RFID chip, which allows radiofrequency radiation identification of the objects carrying a chip, the wearer of the watch should be near an interrogator. In order to transmit information to the interrogator, an RFID tag is generally provided with an electronic chip associated with an antenna.

The means for actuating an alert are triggered when the controller indicates that at least one integrated component in the watch case requires an external intervention for the proper functioning of the watch, in particular a benchmarking of the sensor or a change of the power source.

Figure 7:
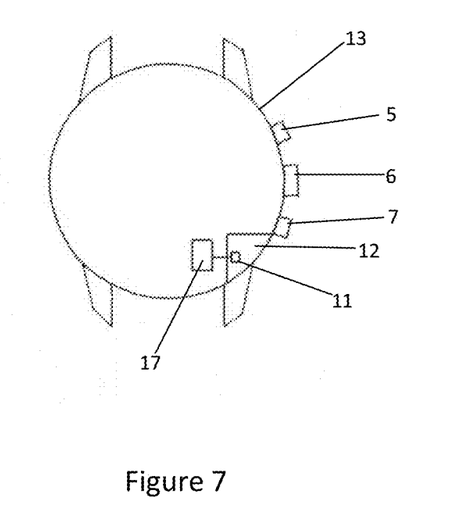
FIG. 7 shows the inside of a watch case of which only the housing in which the sensor is disposed, the sensor itself and a microprocessor connected to said sensor are illustrated.

As illustrated in FIG. 7, the inside of a watch case 13 allows seeing the housing 12, shown schematically, wherein the sensor 11 is disposed, the sensor 11 being connected to the microprocessor 17 containing in particular an internal memory.

The watch includes a conventional sealing device. For example, in the watch illustrated in FIGS. 8 and 9, the watch case 13 includes a container 25 sandwiched between two seals 36 and a sensor support 27 connecting by means of connectors 35 with the container 25. A glass 20 and a back 31 close the watch case 13, the back 31 including a grid for passing a sound emitted by a buzzer 28, a sheet 30 ensuring the sealing between the back 31 grid and an electrical part of the device including in particular the buzzer 28.

Figure 8:
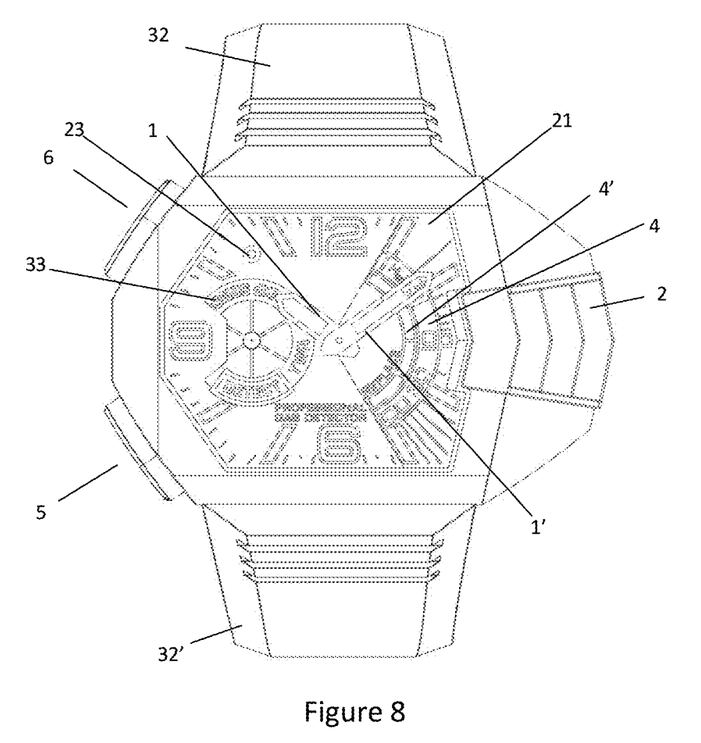
FIG. 8 shows a front view of a wristwatch according to the present invention.
Figure 9:
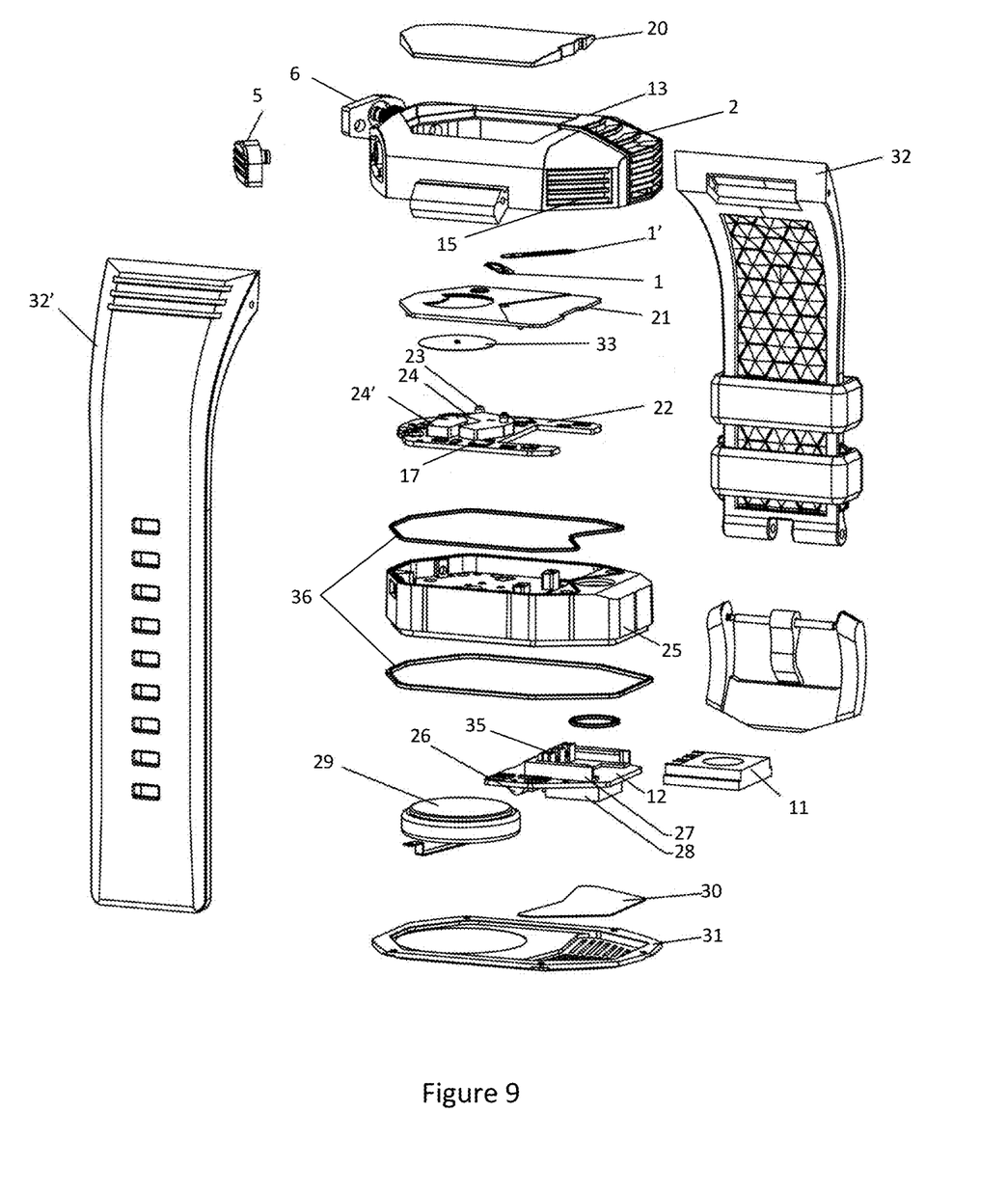
FIG. 9 shows a partial exploded view of the wristwatch of FIG. 8.

As illustrated in FIGS. 8 and 9, a wristwatch according to the present invention includes two push-buttons 5, 6 and a led 23. The watch includes a dial 21 whose first dial area that includes a disk 33 displaying different sizes or operating modes and a second dial area which includes a display of the measurement of each size on two scales 4, 4' by means of hands 1, 1' which also indicate the current time.

Figure 11:
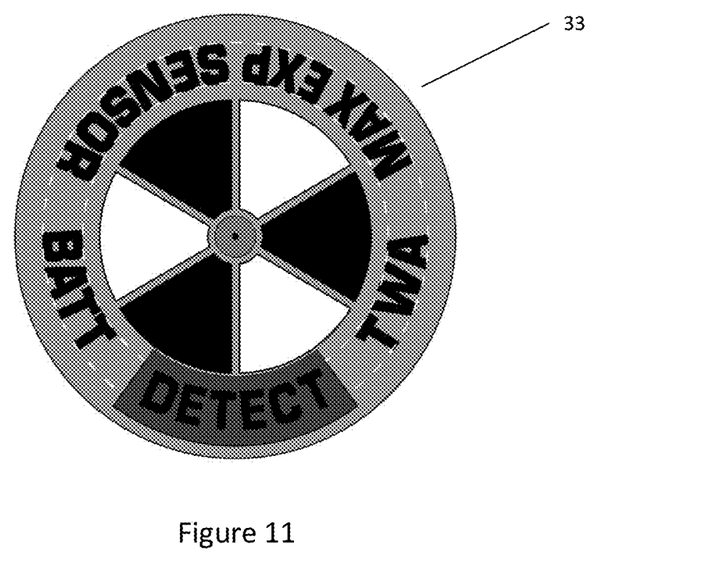
FIG. 11 shows a disk of the wristwatch of FIG. 8.

As illustrated in FIG. 11, the disk 33 includes inscriptions that correspond to sizes to be measured. These inscriptions are written circumferentially on the disk 33 and it is possible, in this example, to distinguish the inscriptions DETECT, TWA, MAX EXP, SENSOR and BATT.

The inscription DETECT corresponds to the index "0" of the disk 33 in the second hand mode when the watch is in normal operation or to an Alarm mode when the watch has detected the presence of a gas. The inscription TWA (Time Weighted Average) corresponds to the time weighted average of gas exposures. The inscription MAX EXP corresponds to the maximum measured value of the gas concentration. The inscription SENSOR corresponds to the lifetime of the sensor. The inscription BATT corresponds to the lifetime of the battery. Other inscriptions can be disposed on the disk 33 such as for example an inscription ALARM which would correspond to the indication of the presence of a gas.

Figure 10:
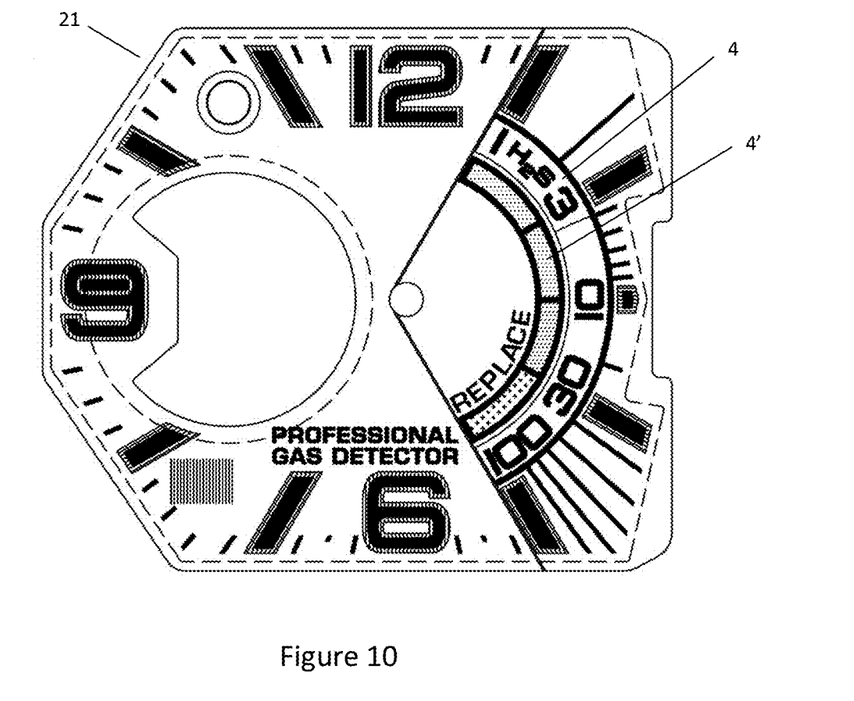
FIG. 10 shows a front view of a watch dial of the wristwatch of FIG. 8.

FIG. 10 allows a better visualization of the dial 21 and in particular the two dial areas, the first which includes an opening for arranging the disk 33 and the second one which includes the display of the measurement of each size on the two scales 4, 4' by means of the hands 1, 1' which also indicate, in the "time" state or mode, the current time. The scales 4, 4' have an arcuate shape. The two scales 4, 4' are concentric about a centre that corresponds to the axis about which the hands 1, 1' turn. The first scale 4, the outermost with respect to the axis of rotation of the hands 1, 1' indicates the gas concentration, here on a scale of 0 to 100. The scale 4 extends over about 120°, about 30° being intended to indicate the nature of the gas, the remainder being reserved to arrange a graduation or an indication of the values. The second scale 4', the closest to the axis of rotation of the hands 1, 1' indicates the lifetime of the sensor or the battery. The lifetime scale 4' extends over about 120°.

As illustrated in FIG. 8, the center of rotation of the disk 33 and the axis of rotation of the hands 1, 1' are aligned in a way that the displayed value represents half of the lifetime. The hour hand 1 indicates the information on the second internal scale 4' and the minute hand 1' indicates the information on the first scale 4. The hour hand 1 is wider than the minute hand 1' of about 10% to 30%, preferably 12%. The minute hand 1' includes a solid part and a perforated part. The perforated part allows reading the information positioned on the first scale 4. The minute hand 1' is longer than the hour hand 1 so that the length of the hour hand 1 corresponds approximately to the solid part of the minute hand 1' so as to always read the information on the first scale 4. Preferably, the hour hand 1 is shorter than the minute hand 1' of about 20% to 30%, typically 25%.

The watch as illustrated in FIG. 8 includes a mechanical display based on hands 1, 1' and a disk 33, the displacement of the hands 1, 1' and of the disk 33 being linked to each other depending on the modes activated by a user of the watch.

The watch includes a Sleep mode, an Alarm mode and a Time mode. The Sleep mode allows deactivating the gas sensor 11. In general, the watch is delivered to a user in the Sleep mode and, in this case, the gas sensor 11 is deactivated, the hands 1, 1' are parked stationary at 9 o'clock and the disk 33 is parked stationary on a SENSOR indication.

In this example, the watch permanently measures the presence of gas in the ambient air. In case of gas detection, the watch automatically switches to the Alarm mode. In the Alarm mode, the disk 33 indicates DETECT. The minute hand 1' displays the current gas concentration on the first scale 4 of gas concentration. The hour hand 1 displays the maximum gas concentration reached. When the gas is no longer detected, the watch automatically switches to the Time mode and the current time is displayed.

In addition to permanently measuring the presence of gas, the watch can display other sizes that should be selected beforehand thanks to the disk 33. For example, it is possible to measure the state of the battery 29, the state of the gas sensor 11, the time weighted average of the gas exposures and the maximum measured value of the gas concentration.

The wristwatch also includes an adjusting mode, indicated on the disk 33 by the indication Detect during which a setting of the time or a benchmarking of the sensor 11 can be carried out.

In this setting mode, in order to activate the watch, it is necessary to simultaneously press the two push-buttons 5, 6 for a given time, five seconds for example. The gas sensor 11 is activated and the wristwatch switches to the Time mode.

In the Time mode, the normal operating mode of the watch, the hands 1, 1' indicate the current time, the disk 33 rotates at the speed of a second hand, namely one revolution per minute, the index 0 is the text DETECT in a window 34.

As previously explained, the watch permanently measures the presence of gas in the ambient air. If case of gas detection, the watch automatically switches to the Alarm mode. When the gas is no longer detected, the watch automatically switches to the Time mode. In the Alarm mode, the minute hand 1' displays the current gas concentration on the scale 4 of gas concentration. The hour hand 1 displays the maximum reached concentration on the scale 4 of gas concentration. In the Alarm mode, a buzzer 28 may emit a sound signal, a vibrator 26 may be triggered at different intervals, and a Led 23 may light up in a fixed manner or by flashing.

In this example, there are four alarm levels depending on the gas concentration in the air measured by the sensor 11, each alarm level emitting a different sound signal, for example 1 beep per minute for a concentration of 1 ppm (part per million or mg·L−1), 2 beeps per minute for a concentration of 5 ppm, 30 beeps per minute for a concentration of 10 ppm and 60 beeps per minute for a concentration of 15 ppm.

When the watch is in the Alarm mode, it is still possible to check the time by pressing the push-button 5. the watch indicates the time and returns automatically to the Alarm mode after a given, for example 10 seconds.

In this example, when the watch has been exposed to a gas, it is possible to consult the two following values:

TWA (Time Weighted Average) is the time weighted average of exposures to the gas.

Maximum exposure, this is the maximum measured value of the gas concentration.

It is possible to consult the TWA and the Maximum Exposure only when the watch is not exposed to a gas.

In order to display the value of TWA, from the Time mode, it is necessary to press the push-button 6 for displaying the TWA. The disk 33 indicates TWA. The two hands 1, 1' are superposed and indicate the TWA on the scale 4 of gas concentration. If the watch has not been exposed to a gas, or if the TWA is less than 1 ppm, the hands 1, 1' are positioned at 12 o'clock.

Pressing simultaneously the two push-buttons 5, 6 for a given time, for example 3 seconds, resets the TWA. From the TWA mode, the watch automatically returns to the Time mode after a given time, for example 10 seconds.

In order to display the maximum value of exposure to a gas, from the TWA mode, the push-button 6 must be pressed. The disk 33 indicates MAX EXP through the window 34. The two hands 1, 1' are superposed and indicate the maximum exposure on the scale 4 of gas concentration. If the watch has not been exposed to a gas, the hands 1, 1' are positioned at 12 o'clock.

Pressing simultaneously the two push-buttons 5, 6 for a given time, for example 3 seconds resets the Maximum Exposure. From the Maximum exposure mode, the watch automatically returns to the Time mode after a given time, for example 10 seconds.

In the example illustrated in FIGS. 8 and 9, two essential sizes can be measured to know their state of operation, in this case, the sensor 11 and the cell 29. Indeed, it is important to know the state of aging of the sensor 11 whose lifetime is generally counted in years and the lifetime of the cell 29 whose lifetime is also counted in years.

The sensor 11 has a lifetime limited in time. After this period, it must be changed. As illustrated in particular in FIG. 9, the sensor 11 is arranged in a support 27 in the manner of a drawer, by sliding in the support 27 until contacting a connector 35 that allows an electrical connection with an electronic board 22. This electronic board 22 includes in particular the microprocessor 17, and two motors 24, 24' arranged to drive in particular the hands 1, 1' and the disk 33.

The sensor 11 having a limited lifetime, it must therefore be changed. After changing the sensor 11, it is necessary to reset the watch. It is possible to consult the lifetime of the sensor 11 and the lifetime of the cell 29 only when the watch is not exposed to a gas.

In order to display the lifetime of the sensor 11, in the Time mode, the push-button 5 must be pressed for displaying SENSOR on the disk 33. The two hands 1, 1' are aligned opposite to each other and the hour hand 1 indicates the aging of the sensor 11 on a second scale 4'. From the SENSOR mode, the watch automatically returns to the Time mode after a given time, for example 10 seconds.

When the sensor 11 reaches its end-of-life, the watch does no longer display time but the disk 33 indicates SENSOR and the hour hand 1 indicates the lowest point of the second ladder 4' (FIG. 10).

In order to display the lifetime of the cell 29, in the SENSOR mode on the disk 33, the push-button 5 must be pressed for displaying BATT (for Battery) on the disk 33. The two hands 1, 1' are aligned opposite to each other and the hour hand 1 indicates the state of the battery on the second scale 4'.

From the BATT mode, the watch automatically returns to the Time mode after a given time, for example 10 seconds.

When the watch receives a shock, it is possible that the disk 33 or the hands 1, 1' lose their alignment. It is then necessary to calibrate them.

In order to calibrate the hands 1, 1' and the disk 33, from the Time mode, the two push-buttons 5, 6 must be pressed simultaneously. A first beep indicates that the watch switches to the Time setting mode.

While maintaining the pressure on the two push-buttons 5, 6, after a defined time, for example 3 seconds, a second beep indicates that the watch switches to the Calibration mode. The disk 33 indicates DETECT and the hands 1, 1' are superposed at 12 o'clock. If the disk 33 is not precisely on DETECT or if the hands 1, 1' are not precisely at 12 o'clock, a calibration is required.

The push-button 6 must then be pressed to turn the hour hand 1 by one step in the clockwise direction or the push-button 5 must be pressed to turn the hour hand 1 by one step in the counter-clockwise direction until the hour hand 1 is precisely aligned with 12 o'clock. The minute hand 1' must be calibrated the same way.

Then, the two push-buttons 5, 6 must be pressed simultaneously in order to calibrate the disk 33. It is necessary to press the push-button 6 in order to turn the disk 33 by one step in the clockwise direction or to press the push-button 5 in order to turn the disk 33 by one step in the counter-clockwise direction until the disk 33 is precisely aligned with the inscription DETECT through the window 34. Pressing simultaneously the two push-buttons 5, 6 completes the calibration.

Without an action, the watch automatically returns to the Time mode after a given time, for example 30 seconds.

As explained previously, when the watch is not used for a long time, or for example when it is sent for maintenance, it is possible to put it in the Sleep mode.

In the sleep mode, the gas sensor 11 is deactivated, the hands 1, 1' are parked stationary at 9 o'clock and the disk 33 is parked stationary on SENSOR. The time is kept by the watch.

For the watch to switch to the Sleep mode, from the Time mode, the two push-buttons 5, 6 must be pressed simultaneously. A first beep indicates that the watch switches to the time Setting mode. The disk 33 indicates DETECT.

Without releasing the two push-buttons 5, 6, after a given time, for example 3 seconds, a second beep indicates that the watch switches to the Calibration mode, the hands 1, 1' are then superposed at 12 o'clock.

Figure 12:
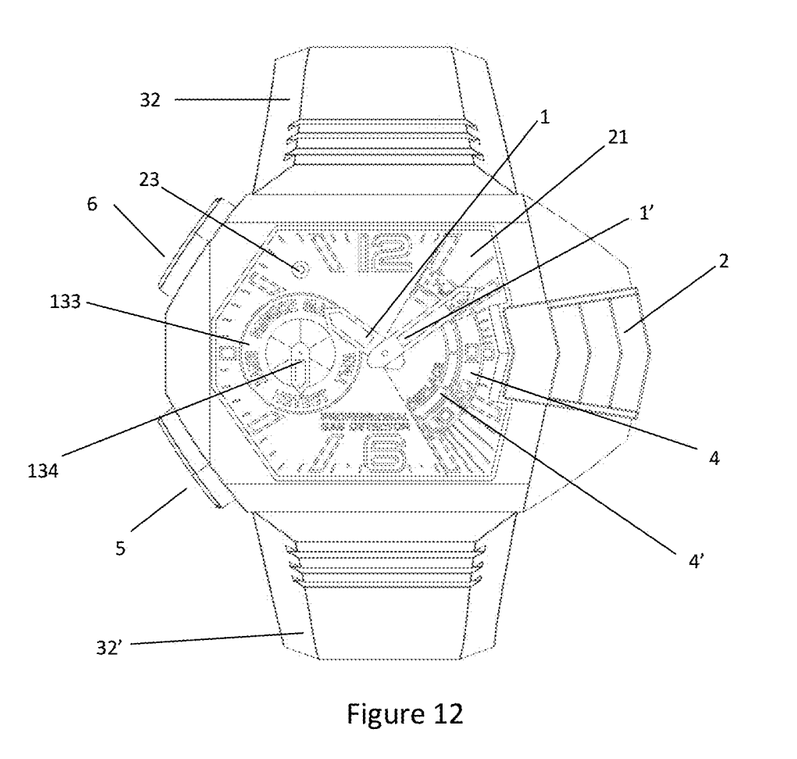
FIG. 12 shows a front view of a wristwatch according to the present invention.

Still without releasing the two push-buttons 5, 6, after a given time, for example 5 seconds, a third beep indicates that the watch switches to the Sleep mode. The disk 33 indicates SENSOR. The two hands 1, 1' are then superposed at 9 o'clock In another version illustrated in particular in FIG. 12, a wristwatch according to the present invention, includes two push-buttons 5, 6 and a led 23. The watch includes a dial 21 whose first dial area that includes a first hand display 133 displaying different sizes or operating modes by means of a hand 134 and a second dial area that includes a display of the measurement of each size on two scales 4, 4' by means of hands 1, 1' which, in the "time" mode also indicate the current time as shown in FIG. 12. Unlike the example of FIG. 8 described previously, the dial 21 and the hand display 133 are one. Thus, the hand 134 rotates at the speed of a second hand in the "Time" mode, namely a revolution per minute. At the user's request, for example for measurements of lifetime of the battery or the sensor, or automatically, for example at the detection of a gas, the hand 134 points to the corresponding mode/state on the first hand display 134.

Therefore, the watch of the present invention allows detecting a gas in an area. However, when the alert means are triggered, it is possible that the wearer of the watch can no longer move because he would for example have fainted. Therefore, the watch includes not only wireless communications means, but also location means. Indeed, it is very important for people who have received an alert to be able to locate the wearer of the watch. The watch can therefore include a pressure sensor 40 through which the watch would be able to know its altitude above sea level with a very high level of accuracy. Thus, the wearer of the watch equipped with the pressure sensor 40 can be found accurately, for example the floor he is located in if he is in a multi-storey building.

In another version of the watch, a simple geolocation sensor can be enough to find the area where the wearer of the watch is without defining the floor if he is in a multi-storey building.

The watch of the present invention is a personal protective equipment that can detect one or more gases allowing to secure an area where the user thereof is located.

The invention claimed is:

1. A device for measuring the concentration of a gas constituent of ambient air, the device including a wristwatch, the device comprising:
    a watch case (13) containing a watch movement, time indicating members (1, 1', 3, 9) visible through a glass of the watch case (13),
    at least one sensor (11) arranged to measure the concentration of a gas constituent of the ambient air, this sensor (11) being located in a housing (12) of the watch case (13) or of an element (14) attached to the watch case and having a surface inside this housing (12) exposed to the ambient air through at least one hole (2), the hole (2) being located on a part of the watch case (13) or on the attached element (14) which, when the wristwatch is worn on a wearer's wrist, is not in contact with the wearer's wrist, a member (4, 4', 8, 9, 10) for indicating the measured value of the gas concentration, and means for actuating an alert; and the device includes two operating states, a time state and an alert state, characterized in that the device is configured to operate according to an entire operational sequence comprising all three of the following steps a), b) and c):

a) in the time state, the members for indicating the time (1, 1', 3, 9) indicate the time and the sensor (11) permanently senses if there is gas or not and measures the gas concentration without displaying it and without actuating an alert in the absence of a measured gas concentration;

b) if the sensor (11) detects a concentration of a gas above a measured value when the sensor is in the time state, the device automatically switches to the alert state wherein the members indicating the time (1, 1', 3, 9) are activated so they indicate the time or inactivated so they do not indicate the time and wherein the member (4, 4', 8, 9, 10) for indicating the measured value of the gas concentration displays this measured value, and furthermore wherein—the means for actuating an alert actuate an alert when the gas concentration measured by the sensor (11) reaches or exceeds a threshold value; and c) in case the sensor (11) no longer detects a concentration of a gas when the sensor is in the alert state, the device automatically switches to the time state in which the members for indicating the time (1, 1', 3, 9) indicate the time and the sensor (11) permanently senses if there is gas or not and measures the gas concentration without displaying it and without actuating an alert in the absence of a measured gas concentration;

and wherein the wristwatch further comprises a wireless communication means for transmitting information to another apparatus, namely the wireless communication means is arranged for transmitting to a smartphone or a computer, information that said threshold value of the measured gas concentration in the ambient air has been reached or exceeded.

2. The device according to claim 1, wherein the members indicating the time are, except as herein specified, non-operational while the device is in the alert state, the device including a control button, operable when the device in the alert state so that these members indicate the time for a predefined period and then the device returns to the alert state.

3. The device according to claim 1, wherein the wristwatch includes a processing unit capable of receiving information from an external apparatus to configure the watch to benchmark the sensor (11) or to update the time.

4. The device according to claim 1, including a processing unit and/or a control unit and/or a storage unit in one or more programmed microprocessors (17).

5. The device according to claim 1, wherein the wristwatch includes a plurality of sensors (11) each arranged to respectively measure the concentration of a particular gas constituent of the ambient air.

6. The device according to claim 1, wherein the wristwatch includes at least one sensor (11) for measuring hydrogen sulfide, or carbon monoxide in the ambient air.

7. The device according to claim 1, wherein a geolocation sensor (40) is arranged to locate the device in a two-dimensional or three-dimensional position.

8. The device according to claim 1, wherein the device also includes a sleep state wherein the sensor (11) is deactivated, and at least one push-button, operable when the device is in the sleep state in order to activate the device in the time state.

9. The device according to claim 1, wherein the means for actuating an alert actuate a multi-level alert depending on the gas concentration in the ambient air measured by the sensor, each alert level corresponding to one or more audible or light beeps or vibrations, whose intensity and frequency can vary.

10. The device according to claim 1, wherein the members indicating the time include a dial and at least two hands (1, 1') of different lengths pivoting about an axis;

the device further comprising a segment of the dial extending up to 150°, this segment of the dial carrying at its periphery at least two arcuate areas with graduations or other indications concerning a measured gas concentration in the ambient air and/or a maintenance operation, these areas being radially shifted;

said at least two hands of different lengths cooperating with the dial to indicate the time during the time state; and said at least two hands of different lengths cooperating with the radially shifted arcuate areas during the alert state to provide at least one indication related to the measured gas concentration in the ambient air or to the measured gas concentration in the ambient air and a maintenance indication.

11. The device according to claim 1, including a dial with a disk carrying at its periphery a series of indications related to: the measured gas concentration in the ambient air, the operation of the device and/or the lifetime of components integrated in the watch case and/or the lifetime of a power source;

the device further including means for rotating the disk or for rotating an indicator member with respect to the disk in order to indicate a chosen indication and, depending on the chosen indication, for operating the device or for calculating different parameters of gas concentration in the ambient air or performing operations necessary to return the device to the operating state.

12. The device according to claim 1, wherein the wristwatch includes an alert means, namely a light alarm (23) and/or an audible alarm (28) and/or a vibrating alarm (26).

13. The device according to claim 1, wherein the wireless communication means of the wristwatch:

is arranged for transmitting information to a control unit arranged to measure the operating state and/or the lifetime of components integrated in the watch case, in particular the sensor (11) or the lifetime of a power source (29); and/or is arranged for transmitting information to a storage unit arranged to keep a history of the measured values of the gas concentration in the ambient air and the measurements of the components integrated in the watch case and inspected by a control unit.

14. The device according to claim 13, wherein said means for actuating an alert are triggered when the control unit indicates that at least one integrated component in the watch case requires external intervention.

15. The device according to claim 1, including:
- a set of hands (1, 1', 3) for displaying the time and—the measured value of the gas concentration in the ambient air, or two sets of hands (1, 3, 18) for displaying these functions separately; or
- a digital display (9) for displaying the time and the measured value of the gas concentration in the ambient air, or two digital displays (9, 10) for displaying these functions separately; or
- a set of hands (1, 3) for displaying the time and a digital display (10) for displaying the measured value of the measured gas concentration in the ambient air or vice versa.

* * * * *